United States Patent
Shah et al.

(10) Patent No.: US 11,553,861 B1
(45) Date of Patent: Jan. 17, 2023

(54) APPARATUS TO DETECT SALT CONCENTRATIONS AND GLUCOSE IN BODILY FLUIDS

(71) Applicant: My Salt and Sugar, LLC, Prospect, KY (US)

(72) Inventors: Riya Shah, Prospect, KY (US); Himanshu Shah, Prospect, KY (US)

(*) Notice: Subject to any disclaimer, the term of this patent is extended or adjusted under 35 U.S.C. 154(b) by 866 days.

(21) Appl. No.: 16/420,986

(22) Filed: May 23, 2019

Related U.S. Application Data

(60) Provisional application No. 62/677,207, filed on May 29, 2018.

(51) Int. Cl.
*A61B 5/00* (2006.01)
*A61B 5/145* (2006.01)
*A61B 5/15* (2006.01)

(52) U.S. Cl.
CPC ...... *A61B 5/14546* (2013.01); *A61B 5/14532* (2013.01); *A61B 5/150748* (2013.01)

(58) Field of Classification Search
CPC .......... A61B 5/14546; A61B 5/150748; A61B 5/14532
See application file for complete search history.

(56) References Cited

U.S. PATENT DOCUMENTS

| | | |
|---|---|---|
| 3,992,158 A | 11/1976 | Przybylowicz et al. |
| 4,329,999 A | 5/1982 | Phillips |
| 4,477,575 A | 10/1984 | Vogel et al. |
| 4,645,744 A | 2/1987 | Charlton et al. |
| 4,960,467 A | 10/1990 | Peck |
| 5,110,724 A | 5/1992 | Hewett |
| 5,300,439 A | 4/1994 | Charlton |
| 5,425,868 A | 6/1995 | Pedersen |
| 5,462,064 A | 10/1995 | D'Angelo et al. |
| 5,465,713 A | 11/1995 | Schoendorfer |
| 5,535,744 A | 7/1996 | DiNino |
| 6,091,975 A | 7/2000 | Daddona et al. |
| 6,503,198 B1 | 1/2003 | Aronowtiz et al. |
| 6,524,864 B2 | 2/2003 | Fernandez Decastro |
| 8,192,360 B2 | 6/2012 | Koh et al. |
| 8,509,867 B2 | 8/2013 | Workman et al. |
| 8,626,453 B2* | 1/2014 | Myoujou ........... A61B 5/14532 700/83 |

(Continued)

*Primary Examiner* — Shogo Sasaki
(74) *Attorney, Agent, or Firm* — Law Office of J. L. Simunic; Joan Simunic

(57) ABSTRACT

The present development is a method and device to monitor the salt level in a patient's blood without the need of laboratory facilities or intervention by medical personnel. The basic device is designed to measure the concentration of analytes, specifically sodium ion and potassium ion, in the patient's blood and to communicate the analyte level to the patient essentially instantaneously through a mobile monitor or display screen. In a variation, the device combines the analyte-concentration measuring function with a means for measuring the concentration of glucose in blood, and the blood analyte level and glucose level are displayed to the patient essentially instantaneously. Both the salt level device and the salt level+glucose level device may be further adapted to allow for the salt and glucose level data to be stored in a data storage base so the patient has an historical record of the concentration levels.

8 Claims, 1 Drawing Sheet

(56) References Cited

U.S. PATENT DOCUMENTS

| | | | | |
|---|---|---|---|---|
| 8,761,940 | B2 * | 6/2014 | Long | G16H 40/63 |
| | | | | 700/83 |
| 8,761,941 | B2 * | 6/2014 | Batman | G01N 33/48785 |
| | | | | 700/83 |
| 8,914,090 | B2 | 12/2014 | Jain et al. | |
| 8,930,028 | B2 * | 1/2015 | McKee | A61B 5/14532 |
| | | | | 702/22 |
| 9,136,939 | B2 * | 9/2015 | Galley | A61B 5/14532 |
| 9,198,623 | B2 * | 12/2015 | Fern | A61B 5/150358 |
| 9,289,165 | B2 | 3/2016 | Soykan et al. | |
| 9,949,672 | B2 * | 4/2018 | Simmons | A61B 5/14532 |

* cited by examiner

APPARATUS TO DETECT SALT CONCENTRATIONS AND GLUCOSE IN BODILY FLUIDS

CROSS-REFERENCE TO PRIOR APPLICATIONS

The present application claims priority to U.S. Patent Application 62/677,207, filed 29 May 2018, and incorporated herein by reference in its entirety.

FIELD OF THE INVENTION

The invention generally relates to devices, systems and methods adapted for use by patients for monitoring their own blood salt levels and their own blood glucose levels without any need of laboratory facilities or intervention by medical personnel.

BACKGROUND OF THE INVENTION

The widespread use of home glucose monitoring and home blood pressure monitoring in recent years has revolutionized the management of diabetes and hypertension. Home monitoring enables patients to track their progress as closely as necessary, at little expense. Self-monitoring also involves patients in their own care, and improves their compliance with prescribed medication.

Similar use of home blood salt level monitoring has been lacking despite such a need for patients to be able to manage the sodium ion and/or potassium ion levels in their blood. Hyponatremia, or a blood sodium level lower than about 135 mEq/L, can result in fatigue, nausea and vomiting, headache, loss of appetite, confusion or disorientation, hallucinations and/or loss of consciousness or coma. Older adults are particularly vulnerable to onset of hyponatremia as a side-effect to use diuretics or antidepressants, heart failure, kidney disease, liver disease or cirrhosis, ketonuria, hypothyroidism, Addison's disease, among other ailments. A blood sodium level greater than about 145 mEq/L, or hypernatremia, can result in excessive thirst, fatigue, swelling in hands and feet, weakness, insomnia, rapid heartbeat, and/or coma. Hypernatremia may result from not drinking enough water, eating too much salt, excessive sweating, diarrhea, low levels of hormones, high levels of aldosterone, Cushing's syndrome, among other ailments.

Currently, blood salt level monitoring normally involves a 24-hour urine collection to measure sodium excretion. But this method has traditionally required the services of a hospital or clinical lab which makes it far too inconvenient for regularly repeated monitoring. Further, it can be difficult or embarrassing for active adults because of the need to carry a bottle all day, remembering to collect urine throughout the day, ensuring that the collected sample is refrigerated in a timely manner, and making a trip to bring each urine collection to the doctor or laboratory.

Thus, it would be beneficial to have a simple salt concentration monitoring system similar to the systems used for glucose monitoring, that a patient could use to determine the concentration of salt in the patient's system quickly and reliably at any point in time. Optionally, the salt concentration monitoring system would also include a functionality to allow for glucose monitoring from a single blood sample so the user can minimize the amount of blood needed for testing and the number of finger pricks to obtain the blood.

SUMMARY OF THE PRESENT INVENTION

The present development is a method and device for use by a patient to monitor the salt levels and glucose levels in the patient's blood without the need of laboratory facilities or intervention by medical personnel. The device combines a means for measuring the concentration of analytes, specifically, sodium ion and potassium ion, with a means for measuring the concentration of glucose in blood, and includes a means for communicating the patient's blood analyte level and glucose level to the patient essentially instantaneously. The present invention is expected to be especially useful for patients with hypertension or congestive heart failure who must control their diets carefully. In an alternative embodiment, the device is adapted to communicate with a data storage base or record-keeping function.

DETAILED DESCRIPTION OF THE PRESENT DEVELOPMENT

The following description is intended to provide the reader with a better understanding of the invention. The description is not intended to be limiting with respect to any element not otherwise limited within this paper.

The present development is a method and a device for assaying the salt concentration, such as sodium ion and/or potassium ion, while concurrently assaying the glucose concentration in a drop-sized blood sample. The method comprises the steps of: (a) obtaining a sample of blood; (b) transferring the blood sample to a sample collector; (c) transferring the blood sample from the sample collector to a filter that is in communication with the sample collector, wherein the filter is configured to remove whole blood cells and solid materials from the blood sample to produce a residual blood serum; (d) transferring a first portion of the residual blood serum to a means for use in the detection of analytes; (e) detecting the presence of analytes and analyzing the concentration of the analytes in the residual blood serum; (f) displaying the analyte concentration as a numerical value on the display panel; (g) transferring a second portion of the residual blood serum to a means for use in the detection of glucose; (h) detecting the presence of glucose and analyzing the concentration of the glucose in the residual blood serum; and (i) displaying the glucose concentration as a numerical value on the display panel.

To perform the method, an exemplary device comprises (a) a means for depositing a blood sample into the device; (b) a means for measuring the concentration of analytes, specifically, sodium ion and potassium ion, (c) a means for measuring the concentration of glucose in blood, (d) a means for transferring the blood sample to the means for measuring the concentration of analytes and the means for measuring the concentration of glucose; and, (e) a means for communicating the patient's blood analyte level and glucose level to the patient.

Figure 1:
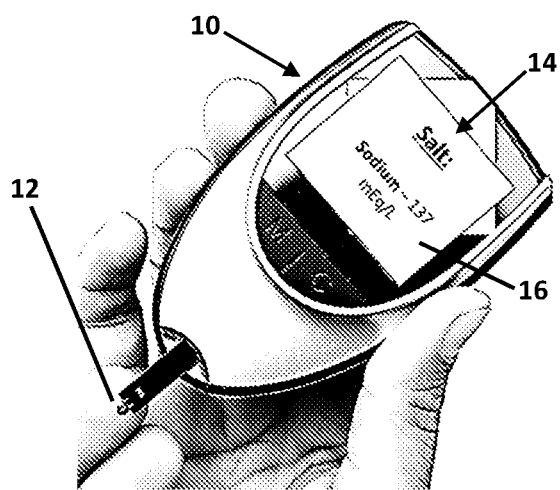
FIG. 1 is a face view of a first embodiment of the present invention wherein blood sodium ion concentration is reported on the display screen.

In a first embodiment, as shown in FIG. 1, the device 10 includes a well 12 that is adapted to receive a blood sample. In a preferred embodiment, the blood sample is a single drop of blood, having a volume less than or equal to 0.1 mL. The blood sample is transferred from the well 12 via capillary flow to and through a filter (not shown) adapted to remove whole blood cells and solid materials from the blood sample to produce a residual blood serum. Capillary flow is described herein as a method of transferring the whole blood through the filter, but it is anticipated that other means of transferring whole blood may be used. The blood serum is transferred from the filter to a test plate (not shown) having at least one test pad (not shown) containing reagent components for use in detection of sodium ion. The blood serum is transferred from the test plate and onto the test pad via capillary flow, although it is anticipated that any other means known for transferring blood serum may be used. The test pad contains a first reagent or first reagent blend for use in detection of sodium ion in blood. Exemplary test plates are described in U.S. Pat. Nos. 4,477,575 and 5,110,724, both of which are incorporated herein by reference in their entireties. Exemplary reagents for reacting with sodium ion include beta-galactosidase and adenosine triphosphatase, although other reagents known in the art may be used.

As further shown in FIG. 1, the device of the present invention provides a screen 14 for displaying the sodium level detected in the blood sample to the patient. In order to display the sodium level, the amount of sodium ion present in the blood sample must be quantified. One exemplary method for quantifying the sodium concentration is by monitoring the changes in the concentration of the first reagent, such as taught in U.S. Pat. No. 4,812,400 which is incorporated herein by reference in its entirety, or by other procedures known in the art. Further as is known in the art, such as taught in U.S. Pat. No. 7,986,986 which is incorporated herein by reference in its entirety, a conversion function module may be used with a calibration set to create a conversion function. The conversion function substantially defines the relationship between the reference analyte data and the analyte sensor data and may be used in a sensor data transformation module to transform sensor data into substantially real-time analyte value estimates, also referred to as calibrated data, as sensor data is continuously (or intermittently) received from the sensor. Optionally, the sensor and/or reference analyte values may be stored in a database for retrospective analysis. The analyte value estimates are displayed to the patient as data output through a user interface 16. In a preferred embodiment, the data output is in the form of a numeric estimated analyte value.

Figure 2:
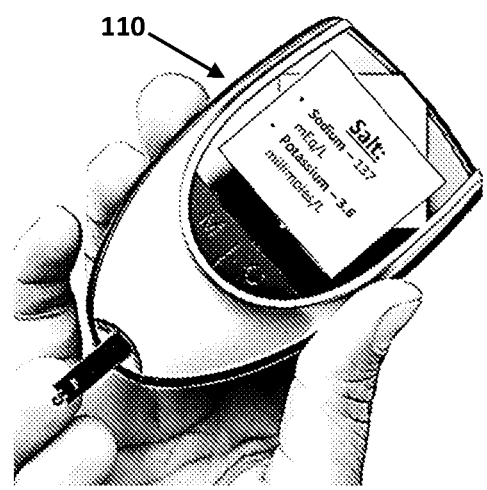
FIG. 2 is a face view of a second embodiment of the present invention wherein blood sodium ion concentration and blood potassium ion concentration is reported on the display screen.

Optionally, as shown in FIG. 2, the assaying device 110 may detect analytes in addition to sodium ion, such as potassium ion. When a plurality of analytes are of interest, the test plate may have at least one, and more preferably a plurality of, wettable, absorbent assay pads, each having an exposed surface region and containing reagents for reacting with a selected analyte, when sample fluid is transferred to the pad, for analyte detection. For example, the reagents selected may be specific for reacting with sodium ion or potassium ion. Exemplary reagents for reacting with sodium ion and potassium ion are taught in U.S. Pat. No. 5,300,439, which is incorporated herein in its entirety by reference.

A color change indicator may also be included in the test pad. Some exemplary indicators include indophenol, 7-(n-decyl)-2,-methyl-4-(3',5'-dichlorophen-4'-one)indophenol, triphenylmethanes, tetra-bromophenolphthalein decyl ester (TBDE), 2-methyl-4-(3',5'-dichlorophen-4'-one)indonaphth-l-ol, fluoresceins, methyl(tetrabromo fluorescein), fluorescein esters, 5 7-hydroxy coumarins, resorufins, pyren-3-ols, flavones, phenolphthalein, bromocresol purple, cresophthalein, chlorophenol red, tetrabromophenol blue, thymophthalein and eosin-5-maleamic acid. If a color change indicator is included in the test pad, the results may be displayed to the patient as the resulting color which would need to be compared to a color scale, or more preferably, the resulting color will be reported in numerical form, such as in the form of a digital readout. A numerical value for the salt concentration may be based on color change by using a color change indicator and an internal colorimeter or by using other spectroscopic methods known in the art and compared to a calibrated standard to generate the analyte value estimate which is used to generate an output as described supra.

In a second embodiment (not shown), the display output is essentially identical to the output shown in FIG. 1 or to the output shown in FIG. 2, depending on whether a single analyte is being monitored or multiple analytes are being monitored, but an alternative method is used for quantifying the analyte concentration. In this second embodiment, the sodium concentration is measured by electrical conductivity or a change in electronic potential by using an internal potentiometer or electrophoresis methods or electrochemical detection methods or ion-transfer differential methods or by any other means that can detect sodium ion and/or potassium ion concentrations and convert the salt concentrations to a numeric value. In a preferred embodiment, the blood serum flows into a sample loading micro-channel, and a first electric field is applied across the sample loading micro-channel to cause the sample to migrate through the loading micro-channel and into a plurality of separation micro-channels that each communicate with the sample loading micro-channel. A second electric field is then applied across the plurality of separation micro-channels to cause a buffer contained in a single buffer reservoir to flow into each of the plurality of separation micro-channels and to cause one or more analytes from said one sample to migrate through the separation micro-channels. The analytes from the sample in a plurality of detection zones are then identified, one each proximate to an end of each of said separation micro-channels using a detector. An exemplary capillary electrophoresis system is described in U.S. Pat. No. 7,988,839 which is incorporated herein in its entirety.

Regardless of the method used for quantifying the sodium or potassium or both sodium and potassium present in the patient's blood, in a most preferred embodiment, the numerical reporting scale will be adjusted to correspond to a standardized scale wherein normal sodium concentration range will be from about 135 mEq/L to about 145 mEq/L, and wherein normal potassium concentration range will be from about 3.5 mEq/L to about 5.0 mEq/L. When referring to blood sodium concentrations, it is generally understood by those skilled in the art that concentrations below about 135 mEq/L indicate potential hyponatremia and readings above about 145 mEq/L indicate potential hypernatremia. When referring to blood potassium concentrations, it is generally understood by those skilled in the art that concentrations between about 5.1 mEq/L to about 6.0 mEq/L indicate potential mild hyperkalemia.

The salt concentration measurement device of the present invention is used by obtaining the device; obtaining a small sample of blood; placing the blood sample in the sample collector; allowing the blood to transfer from the sample collector through the filter to remove whole blood cells and solid materials from the blood sample and to produce a residual blood serum; allowing the blood serum to be analyzed for the presence of sodium ion or potassium ion or both; quantifying the sodium ion or potassium ion or both; and reading the results of the salt concentration test.

Figure 3:
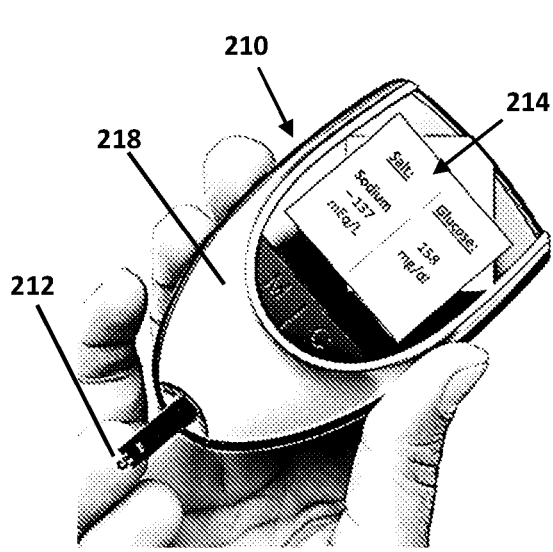
FIG. 3 is a face view of a first embodiment of the present invention wherein blood sodium ion concentration and blood glucose level is reported on the display screen.

In a more preferred embodiment, the device for assaying the sodium ion concentration in a drop-sized blood sample further provides for assaying the glucose level in the same drop-sized blood sample. An exemplary device 210 is shown in FIG. 3. The salt concentration–glucose level device 210 comprises a salt detection portion essentially identical to the previously described device 10 for assaying the sodium ion concentration in a drop-sized blood sample. The glucose level detection portion of the salt concentration–glucose level device 210 comprises a glucose test strip having at least one reagent component for use in detection of glucose, such as glucose oxidase, and a glucometer, as are known in the art. In a preferred embodiment, the glucose level is reported in numerical form, such as in the form of a digital readout, as is known in the art.

Figure 4:
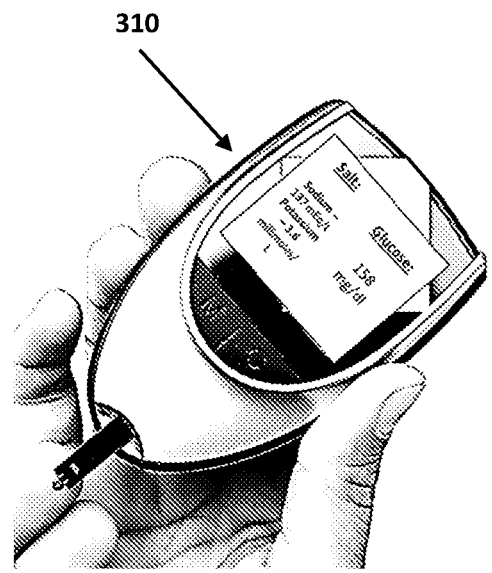
FIG. 4 is a face view of a first embodiment of the present invention wherein blood sodium ion concentration and blood potassium ion concentration and blood glucose level is reported on the display screen.

More specifically, the sodium concentration–glucose level device 210 or, as shown in FIG. 4 the salt concentration–glucose level device 310, comprises a sodium/potassium concentration detection device combined with a glucose monitor in a single housing 218 and with a combined display screen 214. In a preferred embodiment, the salt concentration–glucose level device 210, 310 has a single sample collector 212 adapted to collect a blood sample and to transfer the blood sample to a filter to remove whole blood cells and solid materials from the blood sample to produce a residual blood serum. The sodium/potassium concentration detection section of the device 210, 310 may either comprise a test plate comprising at least one test pad containing reagent components for use in detection of sodium ion or potassium ion, or a sample loading microchannel for electrochemical analysis. The salt concentration–glucose level device 210, 310 further comprises a test plate for the glucose concentration testing in communication with the sample collector wherein the test plate is adapted to receive the blood serum and wherein the test plate comprises at least one test pad containing reagent components for use in detection of glucose level in the blood, and a glucose detection medium, said medium comprising an indicator which produces a visible label in the presence of glucose.

The combination salt concentration–glucose level measurement device 210, 310 of the present invention is used by obtaining the device; obtaining a small sample of blood; placing the blood sample in the sample collector; allowing a first portion of the blood to transfer via capillary flow through the filter to remove whole blood cells and solid materials from the blood sample and to produce a residual blood serum; allowing the blood serum to flow to the analyte detection and quantification portion of the device; reading the results of the salt concentration test; allowing a second portion of the blood to transfer via capillary flow onto a glucose test strip; measuring the glucose concentration with a glucometer, and reading the results of the glucose level test. In a preferred embodiment, the salt concentration and/or glucose level results are read by projecting a numerical value onto a digital output screen wherein the numerical value is displayed on a mobile smart phone, tablet, computer, notepad, IoT hub, connected devices that are Blue Tooth capable or BLE capable, or a combination thereof.

In an alternative embodiment (not shown), the device 10, 110, 210, 310 is adapted to communicate with a data storage base or record-keeping function, such as without limitation, communicating with an application via Bluetooth or WiFi or through wireless communication technology or through wired communication technology. In a second alternative embodiment (not shown), the device 10, 110, 210, 310 is adapted to communicate with a remote device which may be in wireless communication, such as a mobile smart phone, tablet, computer, notepad, IoT hub, connected devices that are Blue Tooth capable or BLE capable, or a combination thereof. It is further anticipated that the blood analyte concentration monitoring device may be modified to detect and quantify analytes other than sodium and potassium commonly present in the blood, such as without limitation lithium, magnesium, calcium, and combinations thereof. If the analyte is detected and quantified by chemical methods, it is anticipated that chemical reagents known to react with the target analyte will be used on the test pad. If the analyte is detected and quantified by electronic methods, it is anticipated that the parameters of the electric fields will be adjusted to complement the analyte of interest.

Specific dimensions relevant to the blood analyte concentration monitoring device of the present invention are provided herein for the purpose of demonstrating the invention, but these dimensions are not intended to limit the scope of the invention. It is understood that, in light of a reading of the foregoing description, one with ordinary skill in the art may make alterations and/or modifications to the present invention, and specifically to the embodiments shown and described herein, without departing from the scope of the invention. For example, those skilled in the art may use different chemical reagents to detect and/or quantify the sodium ion concentration or potassium ion concentration or blood glucose level. It is anticipated that such variations will not depart from the scope of the invention.

Unless defined otherwise, all technical and scientific terms used herein have the same meaning as commonly understood by one of ordinary skill in the art to which the presently disclosed subject matter pertains. Representative methods, devices, and materials are described herein, but are not intended to be limiting unless so noted.

The terms "a", "an", and "the" refer to "one or more" when used in the subject specification, including the claims. The abbreviation "mEq/L" as used herein refers to milli-equivalents per liter.

Unless otherwise indicated, all numbers expressing quantities of components, conditions, and otherwise used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, or percentage can encompass variations of, in some embodiments ±20%, in some embodiments ±10%, in some embodiments ±5%, in some embodiments ±1%, in some embodiments ±0.5%, and in some embodiments to ±0.1%, from the specified amount, as such variations are appropriate in the disclosed application.

All compositional percentages used herein are presented on a "by weight" basis, unless designated otherwise.

The term "analyte" as used herein refers to a substance whose presence or amount in a mixture, suspension or solution is sought to be determined by an analytical method. Analytes of particular interest in the instant case are the sodium ion and potassium ion, each dissolved in a blood serum.

The term "blood serum" as used herein refers to the soluble serum components or the liquid portion of a blood sample that remains after whole blood cells and any other solid materials are removed from the blood sample by filtering the blood sample through a filter material, such as fibrous matrix filter material designed to draw aqueous fluid by surface wetting and to retard the movement of blood cells as the blood sample is drawn through the matrix. The filter materials may be selected from fibrous-mat filters, including cellulose, cellulose acetate, and glass fibrous matrices, or porous substrates, such as sintered glass, fused polymer beads, and the like whose wettability and dimension of interstices are such as to promote movement of an aqueous medium into the matrix by surface wetting.

What is claimed is:

1. A method of monitoring the concentration of analyte and glucose in an individual's blood stream wherein the method comprises the steps of:
   a. obtaining a sample of blood;
   b. transferring the blood sample to a sample collector;
   c. transferring the blood sample from the sample collector to a filter that is in communication with the sample collector, wherein the filter is configured to remove whole blood cells and solid materials from the blood sample to produce a residual blood serum;
   d. transferring a first portion of the residual blood serum to a sample loading micro-channel that is in communication with a plurality of separation micro-channels;
   e. applying a first electric field across the sample loading micro-channel to cause the first portion of the residual blood serum to migrate through the loading micro-channel and into the plurality of separation micro-channels that each communicate with the sample loading micro-channel;
   f. applying a second electric field across the plurality of separation micro-channels to cause a buffer contained in a single buffer reservoir to flow into each of the plurality of separation micro-channels and to cause one or more analytes from the first portion of the residual blood serum to migrate through the separation micro-channels;
   g. identifying the analytes from the first portion of the residual blood serum in a plurality of detection zones, one each proximate to an end of each of said separation micro-channels using a detector;
   h. determining an analyte concentration for each migrated analyte by quantifying the analytes identified in step (g);
   i. displaying the analyte concentration as a numerical value on a display panel;
   j. transferring a second portion of the residual blood serum to a glucose test strip;
   k. allowing the second portion of the residual blood serum to react on the glucose test strip for a predetermined period of time;
   l. determining the concentration of glucose in the second portion of the residual blood serum based on the reaction of the blood serum on the glucose test strip, wherein the glucose concentration is calibrated to generate a digital read-out that reflects the detected glucose concentration in the individual's blood stream; and,
   m. displaying the glucose concentration as a numerical value on the display panel.

2. The method of claim 1 wherein the sample of blood is less than or equal to 0.1 mL.

3. The method of claim 1, wherein the sample collector absorbs a non-dosed amount of blood.

4. The method of claim 3, wherein a portion of the non-dosed amount of blood is filtered and a predetermined quantity of the residual blood serum is delivered to the sample loading micro-channel.

5. The method of claim 1, wherein the migrated analyte is sodium ion, and the sodium ion concentration is displayed in numeric form.

6. The method of claim 5, wherein the numerical value is displayed on a mobile smart phone, tablet, computer, notepad, IoT hub, connected devices that are Blue Tooth capable or BLE capable, or a combination thereof.

7. The method of claim 1 wherein the means for quantifying the glucose concentration is a glucometer.

8. The method of 7 wherein the glucose reading is displayed in numeric form.

* * * * *